United States Patent
Kohl

Patent Number: 5,797,393
Date of Patent: Aug. 25, 1998

[54] METHOD FOR CONTROLLING THE RESPIRATING PHASE IN A VENTILATING APPARATUS

[75] Inventor: Hans-Joachim Kohl, Lübeck, Germany

[73] Assignee: Drägerwerk Aktiengesellschaft, Lübeck, Germany

[21] Appl. No.: 642,761

[22] Filed: May 3, 1996

[30] Foreign Application Priority Data

May 5, 1995 [DE] Germany ............ 195 16 536.5

[51] Int. Cl.$^6$ .................................. A61M 16/00
[52] U.S. Cl. .................. 128/204.23; 128/204.18; 128/204.22
[58] Field of Search ............ 128/204.21, 204.22, 128/205.11, 204.18, 204.23

[56] References Cited

U.S. PATENT DOCUMENTS

| | | | |
|---|---|---|---|
| 3,923,056 | 12/1975 | Bingmann et al. | 128/204.21 |
| 3,961,627 | 6/1976 | Ernst et al. | 128/204.21 |
| 4,957,107 | 9/1990 | Sipin | 128/204.18 |
| 5,582,163 | 12/1996 | Bonassa | 128/204.21 |

FOREIGN PATENT DOCUMENTS 0520082 12/1992 European Pat. Off. ....... A61M 16/00

Primary Examiner—Mickey Yu
Assistant Examiner—V. Srivastava
Attorney, Agent, or Firm—Walter Ottesen

[57] ABSTRACT

The invention is directed to a method for adjusting the respirating pressure during respirating phases in a ventilating apparatus. The method is improved by providing for a volume-controlled ventilation under the conditions of pressure-controlled ventilation as well as allowing for self-respiratory activity. The method includes the steps of: fixing a respirating volume desired value $V_{TS}$ and an inhalation pressure desired value $P_{IS}$; actuating the inhalation valve during inhalation in a first inhalation stroke to adjust the inhalation pressure $P_I$ to the inhalation pressure desired value $P_{IS}$; comparing the respiratory volume $V_T$ to the respirating volume desired value $V_{TS}$ and, if the respirating volume $V_T$ is less than the respirating volume desired value $V_{TS}$, then, during the next inhalation stroke following the first inhalation stroke, incrementally increasing the inhalation pressure desired value $P_{IS}$ by a pressure increment $\Delta P$ until the respirating volume $V_T$ is greater than or equal to the respirating volume desired value $V_{TS}$; and, during each inhalation, comparing the inhalation pressure $P_I$ to the inhalation pressure desired value $P_{IS}$ and, if the inhalation pressure $P_I$ increases to a value greater than $P_{IS}$ because of an intended exhalation, then, opening the exhalation valve to an extent so that the inhalation pressure desired value $P_{IS}$ is reestablished as the inhalation pressure $P_I$.

3 Claims, 1 Drawing Sheet

METHOD FOR CONTROLLING THE RESPIRATING PHASE IN A VENTILATING APPARATUS

BACKGROUND OF THE INVENTION

There are two basic ventilating methods for ventilating patients and are referred to as the so-called pressure-controlled ventilation and the volume-controlled ventilation.

A volume-controlled ventilation requires the adjustment of a tidal volume, a frequency (f) and a ratio of inspiration time to expiration time. The start of a breathing stroke takes place either perforce by a time control or is triggered, that is, triggered by the patient. The inspiration runs with a defined flow pattern and therefore, the required respiratory tract pressure adjusts automatically in dependence upon the flow pattern. The level of airway pressure is essentially dependent upon the elasticity of the lung of the patient but is also influenced by the breathing efforts of the patient.

Monitoring the upper respiratory tract pressure is required in order to prevent the lung from becoming damaged because of a pressure which is too high. Conventionally, the respiratory minute volume is also monitored to control the operation of the respirator. Disadvantages occur from the rigid inspiration flow pattern and the determined minute volume when the patient becomes self active, that is, the patient wants to determine the patient's own flow pattern and respiratory minute volume. The respirator can only react in a limited manner to the self activity of the patient.

A further disadvantage of volume-controlled ventilation is that the constant inspiratory gas flow generates a pressure peak which is reduced by a manually adjustable pressure limitation. The correct adjustment of the pressure limitation is however not entirely without difficulty.

In pressure-controlled ventilation, a fixed respiratory stroke volume is no longer adjusted; instead, so much respiratory gas is metered until a predetermined inspiratory pressure is reached. In many cases, the pressure-controlled ventilating form is more advantageous for the patient than the volume-controlled ventilation. The advantage of the pressure-controlled ventilation is essentially that the patient can control the flow and the volume up to a certain degree by breathing against or breathing with the pressure-controlled ventilation. The pressure-controlled ventilation has however the disadvantage that the minute volume inhaled by the patient must be monitored.

In most recent times, a further form of ventilation has been given considerable attention, that is, free breathing at to a fixed pressure level. In this form of ventilation, the patient is provided with only an increased pressure level to which the patient can inhale and exhale as desired. This increased pressure level is mostly associated with an increased oxygen concentration. In this form of ventilation, it is a precondition that the patient can fully control his or her own ventilation.

European patent publication 0,520,082 discloses a ventilating apparatus wherein a patient is provided with a respiratory gas flow at a fixed pressure level. The respiratory gas flow is increased with a breathing effort of the patient and is reduced when exhaling. This ventilation form is, however, only suitable to support the self breathing activity of the patient. A simultaneous volume control and pressure control is not provided.

SUMMARY OF THE INVENTION

It is an object of the invention to provide a ventilating method which makes possible a volume-controlled ventilation under the conditions of pressure-controlled ventilation and which permits self breathing activity of the patient.

The method of the invention is for adjusting the respiratory pressure during respirating phases in a ventilating apparatus including: an inhalation line; an exhalation line; a respiratory flow sensor for measuring the respirating volume $V_T$ in the exhalation line; an inhalation pressure sensor for measuring the inhalation pressure $P_I$; an inhalation valve for adjusting the respirating gas flow; an exhalation valve for adjusting a preselected exhalation pressure $P_{ES}$ in the exhalation line; and, a central control unit. The method includes the steps of: fixing a respirating volume desired value $V_{TS}$ and an inhalation pressure desired value $P_{IS}$; actuating the inhalation valve during inhalation in a first inhalation stroke to adjust the inhalation pressure $P_I$ to the inhalation pressure desired value $P_{IS}$; comparing the respiratory volume $V_T$ to the respirating volume desired value $V_{TS}$ and, if the respirating volume $V_T$ is less than the respirating volume desired value $V_{TS}$, then, during the next inhalation stroke following the first inhalation stroke, incrementally increasing the inhalation pressure desired value $P_{IS}$ by a pressure increment $\Delta P$ until the respirating volume $V_T$ is greater than or equal to the respirating volume desired value $V_{TS}$; and, during each inhalation, comparing the inhalation pressure $P_I$ to the inhalation pressure desired value $P_{IS}$ and, if the inhalation pressure $P_I$ increases to a value greater than $P_{IS}$ because of an intended exhalation, then, opening the exhalation valve to an extent so that the inhalation pressure desired value $P_{IS}$ is reestablished as the inhalation pressure $P_I$.

The advantage of the invention is that, with each ventilating stroke, the ventilating pressure is increased in a stepwise manner until the preselected breathing stroke volume is applied. An exhalation at the upper pressure level is always possible.

With the ventilating method of the invention, the advantages of the following are combined: the pressure-controlled ventilation by controlling the respiratory pressure, the volume-controlled ventilation by controlling the respiratory volume and free breathing at the particular pressure level.

The ventilation with the ventilating method of the invention takes place essentially as described below.

The ventilation begins first with a test stroke with reduced pressure amplitude, that is, with a reduced inhalation pressure desired value $P_{IS}$. The respirating volume applied hereby is measured during each inspiration and compared to a respiratory volume desired value. If the measured respiratory volume is less than the respiratory volume desired value, the inhalation pressure desired value is increased with the next inhalation stroke and the respiratory volume is again measured. The inhalation pressure desired value is increased until the desired value for the respiratory volume is reached. By limiting the pressure of the respirating stroke, the individual respirating stroke is no longer limited in volume, that is, the patient can demand any desired volume with each individual respirating stroke. It is ensured that the inhalation volume is limited to an adjustable value because of the monitoring of volume which takes place simultaneously. In this way, the freedom of the patient is limited while, on the other hand, a volume trauma is prevented.

If the patient should suddenly start exhaling during inhalation, this is detected from the increase of the inhalation pressure $P_I$ to a value greater than $P_{IS}$. In this case, the exhalation valve is opened to the extent that the inhalation pressure desired value $P_{IS}$ is again established as the inhalation pressure $P_I$.

The ventilating method of the invention can be especially advantageously used with patients having uncontrolled breathing reflexes. With such patients, a conventional minute volume monitoring is ineffective because this monitoring cannot distinguish between the dead space ventilation and the alveolar ventilation. With the ventilating method of the invention, the patient can carry out his or her rough breathing. The foregoing notwithstanding, the minute volume adjusted by the physician is guaranteed for the alveolar range independently of how the lung changes.

In an advantageous manner, the actually measured exhalation pressure $P_E$ is compared to the preselected exhalation pressure $P_{ES}$ during an exhalation which takes place at a preselected exhalation pressure $P_{ES}$. If the exhalation pressure $P_E$ drops below the preselected exhalation pressure $P_{ES}$ as a consequence of an intended inhalation, the respiratory gas flow is increased by means of the inhalation valve in such a manner until the exhalation pressure $P_E$ has again reached the preselected exhalation pressure $P_{ES}$.

BRIEF DESCRIPTION OF THE DRAWING

The single FIGURE of the drawing shows a ventilating apparatus for carrying out the method of the invention.

DESCRIPTION OF THE PREFERRED EMBODIMENTS OF THE INVENTION

Figure 1:
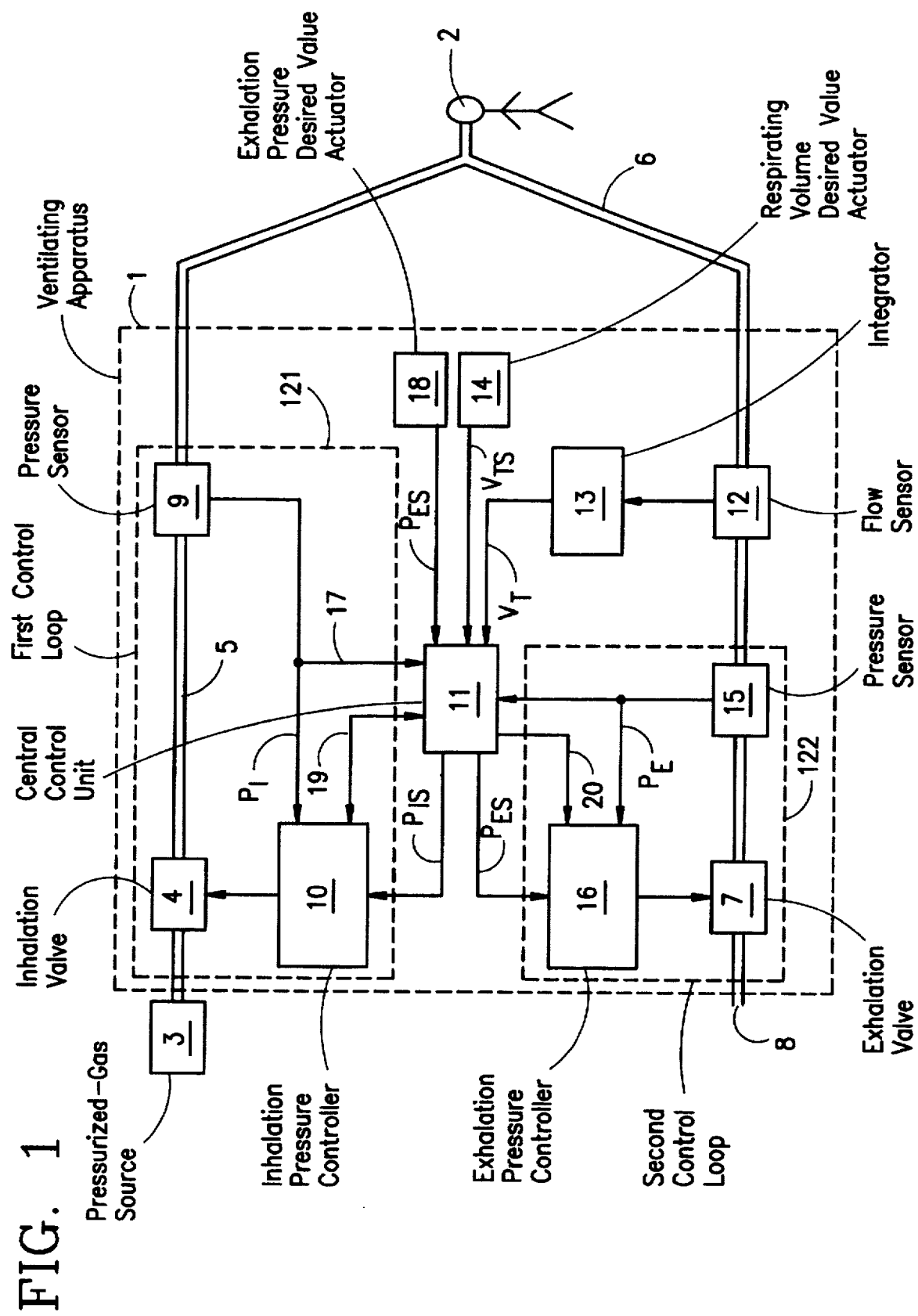

The ventilating apparatus 1 supplies a patient 2 with respiratory gas from a pressurized-gas source 3 via an inhalation valve 4 and an inhalation line 5. The exhaled gas is directed away via an exhalation line 6 and an exhalation valve 7 to an expiration outlet 8. The inhalation pressure in the inhalation line 5 is measured by means of a first pressure sensor 9 and supplied to an inhalation pressure controller 10 as an inhalation pressure actual value $P_I$. The inhalation pressure controller 10 is connected to the inhalation valve 4 which functions as an actuating component to influence the inhalation gas flow. The inhalation pressure controller 10 is connected to a central control unit 11 from which the controller 10 receives an inhalation pressure desired value $P_{IS}$. The inhalation valve 4, the first pressure sensor 9 and the inhalation pressure controller 10 conjointly define a first control loop 121 for adjusting the inhalation pressure $P_I$ to the inhalation pressure desired value $P_{IS}$. The gas flow metered from the pressurized-gas source 3 is adjusted by changing the opening cross section of the inhalation valve 4 in such a manner that the inhalation pressure actual value $P_I$ corresponds to the inhalation pressure desired value $P_{IS}$.

A flow sensor 12 for measuring the volume exhaled by the patient 2 is provided in the exhaust line 6. A measurement signal is supplied by the flow sensor 12 and the respirating stroke volume $V_T$ is computed from this measurement signal in an integrator 13 connected downstream of the flow sensor 12. The respirating stroke volume $V_T$ is supplied to the central control unit 11. The respirating stroke volume $V_T$ is measured in the exhalation line 6 and is proportional to the volume inhaled by the patient 2 if the respirating system is free of leaks which should be a precondition in this case. A respirating stroke volume desired value $V_{TS}$ is inputted into the control unit 11 via a respirating volume desired value actuator 14. A second pressure sensor 15 arranged in the exhaust-gas line 6 measures the exhaled pressure actual value $P_E$ and is connected to an exhalation pressure controller 16. The exhalation pressure controller 16 is connected to the exhalation valve 7 which functions as an actuating component. An exhalation pressure desired value $P_{ES}$ is supplied from the control unit 11 and is fed to the exhalation pressure controller 16 and is there compared to the exhalation pressure actual value $P_E$. The exhalation pressure $P_E$ is adjusted to the value $P_{ES}$ by changing the opening cross section of the exhalation valve 7. The exhalation valve 7, the second pressure sensor 15 and the exhalation pressure controller 16 conjointly define a second control loop 122.

A trigger line 17 is provided for switching over the respirating phases from the inhalation phase to the exhalation phase. The inhalation pressure actual value $P_I$ is fed to the control unit 11 via the trigger line 17.

The method of the invention operates as described below in the context of the arrangement shown in the drawing.

A specific respiratory volume desired value $V_{TS}$ is adjusted by means of the respiratory volume desired value actuator 14. The respiratory volume desired value $V_{TS}$ is read into the central control unit 11. The inhalation pressure controller 10 receives an inhalation pressure desired value $P_{IS}$ from the control unit 11. This inhalation pressure desired value $P_{IS}$ is stored in the control unit. The desired value for the exhalation pressure $P_{ES}$ is adjusted at the respiratory pressure controller 16 via an exhalation pressure desired value actuator 18.

During the first inhalation stroke, the inhalation pressure $P_I$ is set to the start value of the inhalation pressure desired value $P_{IS}$ by means of the inhalation pressure controller 10. The respirating volume exhaled by the patient 2 is measured by the flow sensor 12 and is read into the control unit 11 as respirating stroke volume $V_T$. The respirating stroke volume $V_T$ is compared to the respirating volume desired value $V_{TS}$ in the control unit 11 and, if the respirating stroke volume $V_T$ is less than the respirating volume desired value $V_{TS}$, the inhalation pressure desired value $P_{IS}$ is increased by a preselected pressure increment $\Delta P$ during the next inhalation stroke. The inhalation pressure desired value $P_{IS}$ is increased until the respirating volume $V_T$ is greater or equal to the respirating volume desired value $V_{TS}$. If the inhalation pressure $P_I$ becomes greater than the inhalation pressure desired value $P_{IS}$ during an inhalation (for example, as a consequence of an exhalation intended by the patient 2), a first control signal is outputted to the exhale pressure controller 16 from the control unit 11 via a signal line 20. Via this first control signal, the exhalation valve 7 is opened to the extent that the inhalation pressure desired value $P_{IS}$ is again established as the inhalation pressure $P_I$.

The switchover from inhalation to exhalation takes place in accordance with a time criterion stored in the control unit 11. During exhalation, the preselected exhalation pressure $P_{ES}$ is adjusted by means of the exhalation pressure controller 16 and the exhalation valve 7. The exhalation pressure $P_E$ measured by the second pressure sensor 15 is compared to the preselected exhalation pressure desired value $P_{ES}$ in the control unit 11 and, if the exhalation pressure $P_E$ drops below the preselected exhalation pressure $P_{ES}$ (as a consequence of an intended inhalation), a second control signal is switched to the inhalation pressure controller 10 via a signal line 19. With this second control signal, the inhalation valve 4 is opened so far that the exhalation pressure desired value $P_{ES}$ is again established as the exhalation pressure $P_E$.

With the ventilating method according to the invention, an especially good adaptation to the respiratory effort of the patient is obtained in that during the inhalation, an exhalation to the pressure level of the inhalation is made possible and during the exhalation, an inhalation to the pressure level of the exhalation is made possible.

In an alternate embodiment of the ventilating method for adjusting a predetermined respiratory volume desired value $V_{TS}$, the inhalation pressure $P_I$ is adjusted during inhalation to a fixed inhalation pressure desired value $P_{IS}$ and the exhalation pressure desired value $P_{ES}$ is reduced during exhalation by a predetermined pressure increment $\Delta P$ with each exhalation stroke until the respiratory desired value $V_{TS}$ is reached.

It is understood that the foregoing description is that of the preferred embodiments of the invention and that various changes and modifications may be made thereto without departing from the spirit and scope of the invention as defined in the appended claims.

What is claimed is:

1. A method for adjusting the respiratory pressure during respirating phases in a ventilating apparatus including: an inhalation line; an exhalation line; a respiratory flow sensor for measuring the respirating volume $V_T$; an inhalation pressure sensor for measuring the inhalation pressure $P_I$; an inhalation valve for adjusting the respirating gas flow; an exhalation valve for adjusting a preselected exhalation pressure $P_{ES}$ in said exhalation line; and, a central control unit; and, the method comprising the steps of:

fixing a respirating volume desired value $V_{TS}$;

fixing an inhalation pressure desired value $P_{IS}$ for a first inhalation stroke as a start value;

actuating said inhalation valve during said first inhalation stroke to adjust said inhalation pressure $P_I$ to said inhalation pressure desired value $P_{IS}$;

comparing said respiratory volume $V_T$ at the end of said first inhalation stroke to said respirating volume desired value $V_{TS}$ and, if said respirating volume $V_T$ is less than said respirating volume desired value $V_{TS}$, then, during the subsequent inhalation strokes following said first inhalation stroke, incrementally increasing, in a stepwise manner, said inhalation pressure desired value $P_{IS}$ by a pressure increment $\Delta P$ in each of said subsequent inhalation strokes until said respirating volume $V_T$ is greater than or equal to said respirating volume desired value $V_{TS}$; and, during each inhalation stroke, comparing continuously said inhalation pressure $P_I$ to said inhalation pressure desired value $P_{IS}$ and, if said inhalation pressure $P_I$ increases to a value greater than $P_{IS}$ because of an intended exhalation, then, opening said exhalation valve to an extent so that said inhalation pressure desired value $P_{IS}$ is reestablished as said inhalation pressure $P_I$.

2. A method for adjusting the respiratory pressure during respirating phases in a ventilating apparatus including: an inhalation line; an exhalation line; a respiratory flow sensor for measuring the respirating volume $V_T$; an exhalation pressure sensor for measuring the exhalation pressure $P_E$; an exhalation valve for adjusting a preselected exhalation pressure $P_{ES}$ in said exhalation line; and, a central control unit; and, the method comprising the steps of:

fixing a respirating volume desired value $V_{TS}$;

fixing an inhalation pressure desired value $P_{IS}$ for a first inhalation stroke as a start value;

actuating said inhalation valve during said first inhalation stroke to adjust said inhalation pressure $P_I$ to said inhalation pressure desired value $P_{IS}$;

comparing said respiratory volume $V_T$ at the end of said first inhalation stroke to said respirating volume desired value $V_{TS}$ and, if said respirating volume $V_T$ is less than said respirating volume desired value $V_{TS}$, then, during the subsequent inhalation strokes following said first inhalation stroke, incrementally increasing said inhalation pressure desired value $P_{IS}$ in a stepwise manner by a pressure increment $\Delta P$ in each of said subsequent inhalation strokes until said respirating volume $V_T$ is greater than or equal to said respirating volume desired value $V_{TS}$;

during each inhalation stroke, comparing continuously said inhalation pressure $P_I$ to said inhalation pressure desired value $P_{IS}$ and, if said inhalation pressure $P_I$ increases to a value greater than $P_{IS}$ because of an intended exhalation, then, opening said exhalation valve to an extent so that said inhalation pressure desired value $P_{IS}$ is reestablished as said inhalation pressure $P_I$; and, during an exhalation, comparing the exhalation pressure $P_E$ to the preselected exhalation pressure $P_{ES}$ and, if said exhaled pressure $P_E$ assumes a value less than said preselected exhalation pressure $P_{ES}$ because of an intended inhalation, then:

increasing the respirating gas flow with said inhalation valve so as to cause said exhalation pressure $P_E$ to again at least reach said preselected exhalation pressure $P_{ES}$.

3. A method for adjusting the respiratory pressure during respirating phases in a ventilating apparatus including: an inhalation line; an exhalation line; a respiratory flow sensor for measuring the respirating volume $V_T$; an exhalation pressure sensor for measuring the exhalation pressure $P_E$; an inhalation valve for adjusting the respirating gas flow; an exhalation valve for adjusting a preselected exhalation pressure $P_{ES}$ in said exhalation line; and, a central control unit; and, the method comprising the steps of:

fixing a respirating volume desired value $V_{TS}$ and an inhalation pressure desired value $P_{IS}$;

during an inhalation, adjusting the inhalation pressure $P_I$ to said inhalation pressure desired value $P_{IS}$ by actuating said inhalation valve; and, during an exhalation, determining said respirating volume $V_T$ and comparing said respirating volume $V_T$ to said respirating volume desired value $V_{TS}$ and, if said respirating volume $V_T$ is less than said respirating volume desired value $V_{TS}$, then, during a subsequent exhalation, reducing said preselected exhalation pressure $P_{ES}$ by predetermined pressure increments $\Delta P$ with each exhalation until said respiratory volume desired value $V_{TS}$ is reached.

* * * * *

UNITED STATES PATENT AND TRADEMARK OFFICE
CERTIFICATE OF CORRECTION

PATENT NO. : 5,797,393
DATED : August 25, 1998
INVENTOR(S) : Hans-Joachim Kohl

It is certified that error appears in the above-identified patent and that said Letters Patent is hereby corrected as shown below:

In column 1, line 49: delete "to".

In column 6, line 22: delete "$P_{IS}$," and substitute -- $P_{IS}$ -- therefor.

Signed and Sealed this

Eleventh Day of May, 1999

*Attest:*

*Attesting Officer*

Q. TODD DICKINSON

*Acting Commissioner of Patents and Trademarks*